United States Patent [19]

Condie

[11] 4,296,027
[45] Oct. 20, 1981

[54] PURE INTRAVENOUS HUMAN AND ANIMAL GAMMA GLOBULINS

[75] Inventor: Richard M. Condie, Minneapolis, Minn.

[73] Assignee: The Regents of the University of Minnesota, Minneapolis, Minn.

[21] Appl. No.: 5,150

[22] Filed: Jan. 22, 1979

Related U.S. Application Data

[63] Continuation-in-part of Ser. No. 829,565, Aug. 31, 1977, Pat. No. 4,136,094.

[51] Int. Cl.³ .............................................. C07G 7/00
[52] U.S. Cl. ................................ 260/112 B; 124/101; 124/177
[58] Field of Search ..................... 260/112 B; 424/101

[56] References Cited

U.S. PATENT DOCUMENTS

| | | | |
|---|---|---|---|
| 3,763,135 | 10/1973 | Shanbrom et al. | 260/112 B |
| 3,869,436 | 3/1975 | Falksveden | 260/112 B |
| 3,903,262 | 9/1975 | Pappenhagen et al. | 260/112 B X |
| 3,916,026 | 10/1975 | Stephan | 424/177 |
| 3,966,906 | 6/1976 | Schultze et al. | 260/112 B X |
| 4,021,540 | 5/1977 | Pollack et al. | 260/112 B X |
| 4,075,193 | 2/1978 | Campbell et al. | 260/112 B |
| 4,087,519 | 5/1978 | Trepo | 260/112 B X |
| 4,093,606 | 6/1978 | Coval | 260/112 B |
| 4,124,576 | 11/1978 | Coval | 260/112 B |
| 4,126,605 | 11/1978 | Schneider et al. | 260/112 B |
| 4,136,094 | 1/1979 | Condie | 424/101 X |
| 4,154,819 | 5/1979 | Stephan | 424/101 |
| 4,160,763 | 7/1979 | Müller | 260/112 B |
| 4,164,495 | 8/1979 | Hansen | 260/112 B |
| 4,168,303 | 9/1979 | Nishida et al. | 260/112 B X |

OTHER PUBLICATIONS

The Proteins, vol. II, p. 25, Third Edition, 1976, Neurath et al.
Vox Sang. 32:175–181 (1977), Masuho et al.
Monogr. Allergy, vol. 9, pp. 39–60 (1975), Barandun et al.

*Primary Examiner*—Howard E. Schain
*Attorney, Agent, or Firm*—Burd, Bartz & Gutenkauf

[57] ABSTRACT

Isolated and purified natural, unaltered, undenatured immune gamma globulin (IgG) for intravenous administration prepared from animal blood plasma, especially human. The products are characterized by high yield and high purity. They are unfragmented and unaggregated, i.e., natural preparation.

9 Claims, 2 Drawing Figures

PURE INTRAVENOUS HUMAN AND ANIMAL GAMMA GLOBULINS

This application is a continuation-in-part of my prior application Ser. No. 829,565, filed Aug. 31, 1977, now U.S. Pat. No. 4,136,094, issued Jan. 23, 1979.

BACKGROUND OF THE INVENTION

FIELD OF THE INVENTION

The invention relates to isolated and purified natural, unaltered, undenatured immune gamma globulin prepared by the fractionation of animal blood plasma. More particularly, the invention relates to intravenously injectable human immune gamma globulin.

SUMMARY OF THE INVENTION

In my aforesaid copending application Ser. No. 829,565, U.S. Pat. No. 4,136,094 whose disclosure is incorporated herein by reference, there is described and claimed a method for producing the intravenous gamma globulins of the present invention. The products are "native", natural, undenatured, aggregate-free, sterile, free from virus and can be isolated in higher yields than with the alcohol fractionation method and in a purer state.

The method involves three basic manipulations. The first step: plasma stabilization, the second: isolation and elution from ion exchange resins of gamma globulin and albumin, and the third step: concentration, dialysis and sterile filtration. The plasma stabilization step comprises treatment with fumed colloidal silica by admixing plasma with silica and then separating stabilized plasma from the silica with adsorbed constituents. The stabilization accomplishes removal of a number of aggregable and easily denaturable plasma proteins. Also removed are the hepatitis associated antigen in plasma and a number of proteolytic enzymes and their precursors, which can lead to the degradation and aggregation of other plasma proteins and the activation of the kinin system.

The second step involves the isolation of the IgG and albumin from the stabilized plasma by reacting this material with a sterile ion exchange resin. The IgG and albumin are eluted by adjustments of pH and ionic strength. In addition, pyrogenic activity of plasma is removed by these resins. This ion exchange separation step results in the isolation of an undenatured, monomeric (molecular weight 160,000) aggregate free human IgG 99% pure, with yields of between 60-70%. The I.V. IgG contains less than 1% aggregates and less than 1% dissociated materials. The final step involves the concentration, dialysis, and sterile filtration of the IgG and albumin.

The final products have been subjected to the standard quality control tests that have been set forth by the Bureau of Biologics. These tests include testing for sterility, pyrogenic activity, and toxicity. In addition, tests for aggregation, deaggregation and molecular weight have been performed. Finally, these materials have been tested for and shown to be free of hepatitis associated antigen, by radio immunoassay. Intravenous administration of large quantities (over 30 grams) in over 50 patients has shown no evidence of passage of hepatitis virus nor produced cases of hepatitis.

Blood plasma of man and mammals contains more than 100 proteins, many of which do not have as yet recognized functions. Some of these proteins are components of multi-enzyme systems such as the complement pathway, blood coagulation, and the fibrolytic and kininogen systems. Other plasma protein systems of great physiologic and medical importance include the immunoglobulins. The immunoglobulins differ from all other plasma proteins in their multiplicity, their heterogeneity, their genetic control, their antibody specificity, and their biologic effector functions. Immunoglobulins are defined as multifunctional proteins that are endowed with both known antibody specificity and biologic effector functions. Further immunoglobulins are endowed with structural features that control and orchestrate a number of critical biologic effector mechanisms through interactions with the complement, fibrinolytic, coagulation, and kininogen system of the blood plasma. Whether these biologic effector functions serve the host or result in harmful systemic reactions is determined by the state of the immunoglobulin molecule. Native immunoglobulins serve the host under normal conditions whereas altered or denatured immunoglobulins result in the generation and triggering of potent, damaging systemic reactions.

Immunoglobulins are formed by the lymphoid cell system of vertebrates and circulate in the blood plasma. They migrate electrophoretically as gamma globulins, but usually are very heterogenous, ranging to the beta globulins. There are five classes of immunoglobulins with the IgG class making up the majority of the circulating immunoglobulins as well as containing the majority of the specific protective antibodies in the immunoglobulins of the plasma.

Isolation and purification of the native IgG protein from the over 100 different proteins in plasma has presented as yet unresolved major obstacles in protein fractionation. These include isolation of the IgG molecule in its native state free of denaturation, and isolation in a highly purified state free of any fragments or activated peptides that have been shown to develop during various fractionation procedures. (Activated peptides have marked pharmacologic effects when injected into man and can produce severe reactions at nanogram levels. Denatured IgG activates the complement pathway, portions of the blood coagulation and kininogen systems resulting in the production of severe systemic reactions.)

CURRENT LICENSED PROCEDURE FOR FRACTIONATION OF HUMAN IgG

The only licensed procedure for the fractionation of human plasma at the present time is the Cohn cold alcohol method. This procedure results in the separation of the three major blood proteins for therapeutic use: albumin—the major regulator of osmotic pressure and plasma; fibrinogen—principle in the blood coagulation system; and gamma globulins—the antibody containing fractions. Fractionation of proteins by this process and others involving protein precipitants or ion exchange chromatography have met with limited success. A significant body of evidence has accumulated which demonstrates that the proteins isolated are not natural, native products, but have been denatured extensively. The Cohn cold ethanol method depends upon balancing the precipitating action of the organic solvent with the solvent actions of the electrolytes present while controlling for five independent variables, namely electrolyte concentration, alcohol concentration, hydrogen ion concentration, temperature, and protein concentration. To the extent that these variables are controlled depend the purity, yield, and the extent of denaturation of each plasma protein isolated.

Gamma globulins and IgG isolated by these precipitation or ion exchange methods must be administered intramuscularly. Intravenous administration results in a series of undesirable side effects which include erythema, vomiting, abdominal pain, fever, collapse and loss of consciousness. In marked contrast, the native IgG of fresh human plasma may be administered intravenously with no untoward reactions. Therefore, the methods to isolate a native product must produce an IgG that has the same if not similar properties of IgG in fresh plasma.

PRESENT KNOWLEDGE OF THE NATIVE IgG MOLECULE

While extensive, detailed information has been published characterizing the primary, secondary, tertiary, and quaternary structure of the IgG molecule, no documentation exists demonstrating that IgG isolated and utilized in these structural studies retains its biological effector function similar to that of the native molecule of fresh plasma. The standards for characterization of the isolated native IgG molecule must therefore include not only structural details, but comparative evidence of its biologic behavior with reference to the native IgG in fresh plasma.

These biologic and structural parameters include: (1) native electrophoretic range, (2) native IEP (isoelectric point) range, (3) evidence that neither new chemical groupings have been added nor native chemical groups removed or altered, (4) one-half time or turnover time in the circulation of three weeks, (5) low anticomplementary activity, (6) molecular weight of 160,000, (7) no aggregates or low molecular fragments, (8) resistance to limited proteolysis (indicative of a non-denatured native state), (9) free of partial proteolytic damage by activated plasma plasmin, and (10) safe for intravenous injection in large quantities.

Stated differently, intravenous infusion of fresh plasma is safe, the IgG is not anticomplementary, and has a turnover of approximately three to four weeks. When plasma is fractionated by the current licensed cold ethanol procedure of E. J. Cohn, by ammonium sulfate precipitation, by ethylene glycol precipitation, or by a combination of these or with DEAE ion exchange chromatography, the IgG isolated does not retain the same physiologic characteristics it possessed while part of the fresh plasma. Upon intravenous administration, these preparations frequently result in fever, abdominal pain, vomiting, loss of consciousness, and circulatory collapse. Over 25% of the injected material is cleared from the circulation within minutes, with the remainder having a turnover time of less than three weeks. All of the above fractionation procedures, while isolating and concentrating the predominant neutralizing/protective antibodies as evidenced by in vitro neutralizing assays, impair the biologic effectiveness of the IgG molecule by virtue of altering the native physiologic state of IgG. The IgG isolated contains aggregated IgG, in quantities which indicate extensive denaturation. Up to 25% of IgG aggregates are contained in commercial preparations as well as by those prepared on a small scale. During the isolation procedure there is also evidence that plasminogen of plasma is activated to plasmin and has partially degraded the IgG molecule, leading to aggregation and structural alterations reflected by alterations in effector functions of the IgG molecule. These include altered anticomplementary activity, shortened turnover time or half life, and activation of the blood coagulation and kininogen systems in the body on intravenous injection resulting in a shock-like syndrome.

STRUCTURE AND FUNCTION OF THE IgG MOLECULE

The IgG molecule has a molecular weight of 160,000 Daltons. It is predominantly protein, but contains 3% carbohydrate. IgG differs from protein enzymes which have served as model proteins in that IgG molecules are biologically active proteins carrying out many different biologic functions. These biological functions include the primary function—combination of the IgG molecule with antigen, and secondary or effector functions such as immunoglobulin or IgG turnover, placental and gut active transport of the IgG molecule, activation of complement by the IgG molecule, cytophilic reactions involving the IgG molecule, metabolism and transport of the IgG molecule including functions which determine its half life in the circulation, and finally complement fixing mechanisms.

PRIMARY AND SECONDARY STRUCTURE

The IgG molecule can be regarded as derived from a basic structure of two light polypeptide chains and two heavy polypeptide chains linked together by covalent bridges of cystine residues. The four chains are paired so that the molecule consists of two identical halves, each of which has one heavy and one light chain. By amino acid sequence analysis, it is shown that both heavy and light chains have regions in the N-terminal portion with highly variable amino acid sequences and regions in the carboxy terminal end with constant amino acid sequences.

TERTIARY STRUCTURE

Considerable evidence from a variety of chemical and physical studies indicates that the heavy and light chains are folded into a linear series of compact globular regions called domains. The light chain is composed of two domains: one corresponding to the variable amino acid sequence region, the $V_L$, and the second is the constant amino acid sequence region, the $C_L$. In the heavy chains there are four domains, one formed by the variable region, $V_H$, and three by the constant homology region, $C_{\gamma 1}$, $C_{\gamma 2}$ and $C_{\gamma 3}$. Each three dimensional domain corresponds approximately to 110 amino acid residues, contains a single intrachain disulfide bond, and is linked to the neighboring domains by more loosely folded stretches of polypeptide.

CORRELATION OF STRUCTURE WITH BIOLOGIC FUNCTION

As a corollary to this structural model, it has been proposed that each domain evolved to perform specific functions, and thus the $V_L$ and the $V_H$ jointly form the antigen binding site where the constant region domains, particularly in the FC region, the $C_{\gamma 2}$ and $C_{\gamma 3}$, mediate the biologic effector functions of the immunoglobulin molecule. There is evidence which supports this concept of structural differentiation of the IgG molecule, and more specifically, that this modular structure is accompanied by functional differentiation within the IgG molcule. A number of investigations have shown that most of the interactions with the non-specific or effector mechanisms of the body occur through the FC region in the molecule. In some cases the locations of these sites have been precisely defined. For example, it has been shown that the $C_{\gamma 3}$ domain is involved in the histamine release for mast cells in heterocytotrophic passive cutaneous anaphylaxis and in the binding to heterologous and homologous macrophages. It has also been determined that the site controlling catabolic rate, antibody dependent cytotoxicity, and complement fixation are likely to be associated with the $C_{\gamma 2}$ domain or to depend on the presence and the integrity of both domains since these activities are not displayed by isolated $C_{\gamma 3}$, or the PFC.

NATIVE, UNDENATURED MOLECULES REQUIRED FOR FULL NORMAL BIOLOGIC ACTIVITIES

The domain hypothesis proposes that the homology regions of the immunoglobulin molecule have evolved independently to perform separate functions. More recent work suggests that the roles played by the individual domains and the mediation of effector functions are in many cases more complex than those envisioned in the domain hypothesis. Although some functions such as $C^{1Q}$ binding require only one domain, other activities are dependent upon higher orders of structure involving pairs of domains, or more likely the native conformation of the complete IgG molecule.

Finally, there is strong evidence to indicate that minor modifications in the domain structure resulting from methods of fractionation or from limited proteolysis by proteolytic enzymes alter the IgG molecule from its native, physiologic state in the blood and result in marked alteration in complement binding, anticomplementary activity, and turnover rate.

ISOLATION AND PURIFICATION OF THE NATIVE IgG MOLECULE

Methods to isolate IgG from plasma in its native, physiologic state must take into consideration conditions when denaturation occurs and must take into account specifically the area or areas of the IgG molecule most susceptible to alteration. The heavy chains of the IgG molecule contain a length of polypeptide chain, between the $C_{\gamma 1}$ and $C_{\gamma 2}$ domains, known as the hinge region. In this region there is flexibility between the antigen combining region (FAB) and the complement fixing segment (FC). The hinge region is rich in proline amino acid residues and contains the inter-heavy chain disulfide bridges. Under conditions of controlled denaturation, IgG can be enzymatically cleaved at points lying between domains in preference to those lying within domains. (This suggests that domains form a relatively compact structure joined by short sections of looser structure.) The hinge region appears to be the most susceptible part of the molecule to denaturation and enzymatic cleavage. Fragmentation with papain, pepsin, or plasmin has generally been used.

The IgG antibody molecule's primary function, namely its combination with antigen which occurs in the FAB portion, is most resistant to denaturation (or other conditions altering shape or causing change within the molecule). While the primary function remains unaffected by denaturation, the hinge region and constant domains of the FC region are markedly altered, an effect reflected by marked changes in such biologic effector functions as IgG turnover rate, metabolism, and complement fixation, and normal interactions with the complement pathway, the coagulation, fibrinolytic, and kininogen systems. In the past undue weight has been given to the fact that IgG molecules isolated by many different methods are still able to interact with antigen in an apparently unimpaired, native way. More attention must be given to the extensive evidence that other functions of the IgG molecule have been markedly impaired by alcohol fractionation, ammonium sulfate salting out method, polyethylene glycol method, etc., methods that all isolate IgG with little impairment in its ability to combine with antibody, but have marked denaturating effects on the other portions of the molecule. Denaturation as reflected by the presence of up to 25% aggregates, significantly decreases half life in the circulation, and significantly increases complement fixing activity.

STANDARDS FOR THE NATIVE ISOLATED IgG MOLECULE

The standards characterizing the native IgG molecule must include comparisons with IgG prepared by the current and prior art with IgG prepared by the method claimed in my aforesaid application Ser. No. 829,565 with final proof resting on the determinable characteristics and properties of the molecule in fresh plasma. While some modifications of IgG from its native state can be directly demonstrated by structural studies and in vitro tests of biological effector functions, the final definition of its native state must include purity and structural analysis, coupled with comparative studies between the different IgG's and IgG in fresh human plasma particularly when each is intravenously administered.

Purity—The current standards of purity whereby contaminants present in no lower than microgram concentrations are identified cannot be used since it has been demonstrated that the current IgG preparations contain nanogram quantities of peptides with potent pharmacologic activity. The administration of these materials produce severe vasoactive reactions. Therefore the purity standards for native, non-denatured monomeric IgG must be at lower levels to include an analysis of these substances.

Structural Analysis—Structural parameters defining altered or denatured IgG are at best rather ill defined, but include such gross characteristics as: (1) molecular weight characterization of the different molecules making up the IgG preparation including both high molecular weight aggregates and low molecular weight fragments, (2) anti-complementary activity, (3) native electrophoretic mobility ranges, (4) native isoelectric point ranges, and (5) demonstrating that the monomeric 160,000 molecular weight IgG molecules are resistant to limited proteolysis by plasmin.

In Vivo Characterization—The denatured non-native IgG molecule exhibits a number of altered biologic effector functions. Behavior of such IgG in the circulation of the body can only be assessed by comparative in vivo studies involving intravenous administration of both the IgG of fresh plasma and the purified IgG preparation. These include: (1) demonstration that the preparation is safe for intravenous administration in quantities of up to 200 mg/kg and does not produce either circulatory collapse, fever, pain, vomiting, or activate the kinin in the complement systems, and (2) half-life or turnover times similar to IgG of normal plasma.

While some modifications of the IgG molecule from the native state can be directly demonstrated by structural studies and in vitro testing, the final definition of the native molecule must include both structural and biologic evidence that on intravenous administration the IgG molecule behaves in a similar way to the IgG of fresh human plasma. The structural parameters denoting the native, undenatured, unaltered IgG molecule include: (1) native electrophoretic ranges, (2) native isoelectric ranges, (3) molecular weight of 160,000 Daltons with no aggrevated IgG and no IgG fragments, (4) low anti-complementary activity, and (5) resistance to limited proteolysis with plasmin. The biologic indicators denoting the native, undenatured, unaltered IgG molecule include: (1) normal half-life or turnover time following intravenous administration of three weeks, (2) no evidence of early accelerated (within minutes) phase of rapid clearance following intravenous administration (indicative of IgG partially degraded by plasmin and aggregated IgG), (3) safe for intravenous administration in large quantities (200 mg/kg) in the clinical setting (with clearly demonstrated freedom from untoward reactions such as fever, vomiting, loss of consciousness, etc.), and (4) free of properties activating the complement pathway, the blood coagulation and kininogen system.

BRIEF DESCRIPTION OF THE DRAWINGS

The invention is further illustrated by the accompanying drawings in which:

FIG. 1B representative of elution curve of human IgG prepared by alcohol fractionation followed by reduction and alkylation;

FIG. 1C is a protein elution curve from a Biogel column of a fractionated human IgG that has been treated with $\beta$ propiolactone;

FIG. 1D is a representative elution curve characteristic of IgG prepared by methods involving ethyl alcohol precipitation, ethylene glycol precipitation, and salting out procedures;

FIG. 1E is an elution curve from an ethyl alcohol fractionated IgG that has been degraded by plasmin activated during the fractionation procedure;

FIG. 1F is an elution curve of alcohol precipitated IgG analyzed in total protein to determine the distribution of various molecules, and concentration of the various peaks in terms of IgG, A, and M.

CHARACTERIZATION OF THE AGGREGATION, FRAGMENTATION AND SHAPE CHANGE OF THE VARIOUS IgG PREPARATIONS WITH COMPARISON TO NATIVE IgG

Exclusion chromatography using acrylamide copolymer beads (Biogel A 1.5) was selected as the method to determine the number of different molecular weight components in each IgG preparation and to determine if possible detectable changes in molecular shape. Since plasma contains numerous different proteins with molecular weight similar to the 160,000 Dalton IgG, the prototype for the native IgG was prepared from human plasma by the method incorporated in my aforesaid application Ser. No. 829,565. Comparisons under identical conditions of protein concentration, gel type, column diameter and length, etc. were made with a representative ethanol fractionated IgG, with a reduced and alkylated intravenous IgG, with chemically altered $\beta$ propiolactone treated IV IgG and an ethanol precipitated plasmin degraded IgG. Quantitative assessment of the percent aggregation, percent fragments and alterations in molecular shape were determined by placing 2 ml samples of IgG at a concentration of 45 mg/ml over a Biogel A 1.5 column. The column was 2.6 cm in diameter by 94 cm in length. The emerging protein was collected in 7 ml aliquots and protein concentration determined by absorbance at 280 millimicrons or by quantitative determination of IgG content in Mancini plates.

With this method molecular weights plus molecular shape and hydration affect the behavior of molecules during chromatography. In general, protein molecules appear in the column eluate in order of decreasing size. The columns used had been standardized and calibrated for molecular weight determination using a number of different standardized protein molecules.

Figure 1:
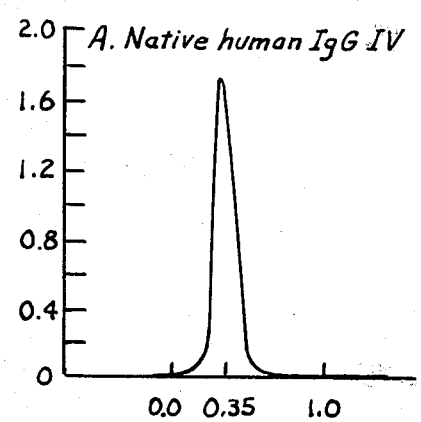
FIGS. 1A through 1F represent the elution curves derived from chromatographic analysis of various IgG preparations compared to native IgG, FIG. 1A constituting the prototype for native human IgG.
Figure 1:
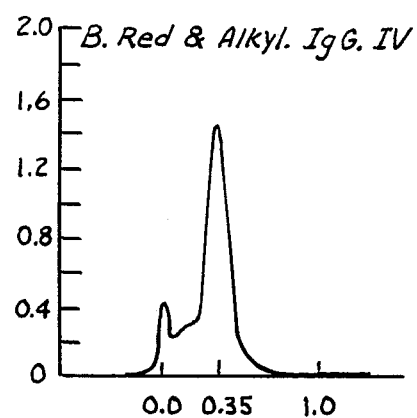
Figure 1:
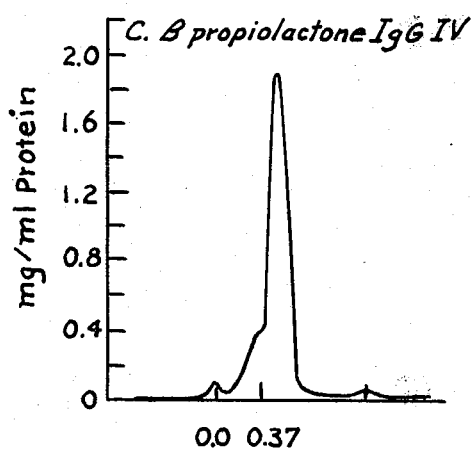
Figure 1:
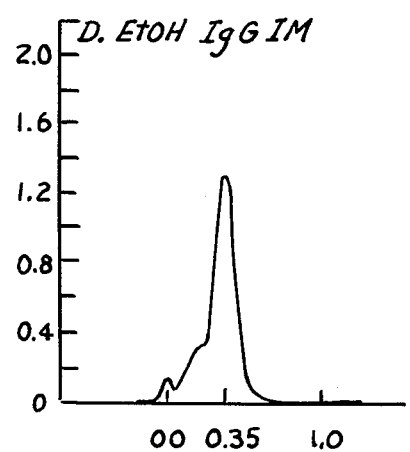
Figure 1:
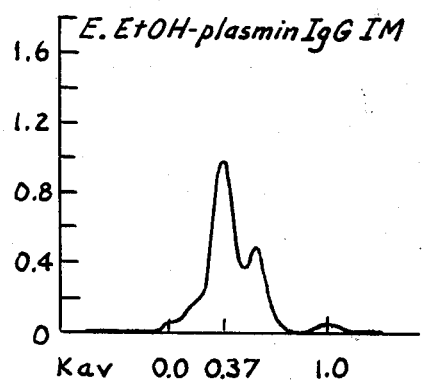
Figure 1:
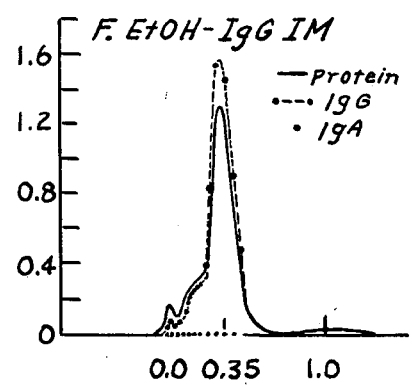

FIG. 1A represents the elution curve derived from this type of structural analyses and constitutes the prototype for native human IgG. The IgG was prepared by the method incorporated in application Ser. No. 829,565. The protein elution curve is symmetrical indicating monomeric molecular species of identical shape and volume. Aggregates constitute less than 1% of the total protein eluted. Fragmented IgG also constitutes less than 1% of the total protein added. The protein elution curve is consistent with a monomeric, unaggregated, unfragmented native IgG. This elution curve is to be contrasted with the elution curve for the following non-native IgG preparations.

FIG. 1B is representative of elution curve of human IgG prepared by alcohol fractionation followed by reduction and alkylation. The elution is not symmetrical. High molecular weight aggregates constitute 20% of the total protein of this preparation with a very high percent of high molecular weight (over 1,000,000) aggregates.

FIG. 1C is a protein elution curve from a Biogel column of a fractionated human IgG that has been treated with $\beta$ propiolactone. This IgG contains over 14% aggregates, some consisting of very high molecular weight materials. It also contains detectable levels of fragmented 50,000 molecular weight IgG (2.5%). The main peak rather than being symmetrical is altered and consists of only 83% of the total protein.

FIG. 1D is a representative elution curve characteristic of IgG prepared by methods involving ethyl alcohol precipitation, ethylene glycol precipitation, and salting out procedures. Protein concentration, elution and column dimensions are identical on all runs. The protein elution curve is not symmetrical. Sixteen percent of the total protein is composed of various high molecular weight aggregates. These aggregates include dimers, trimers, tetramers, and molecular aggregates greater than 1,000,000 molecular weight. There are not appreciable quantities of fragmented IgG in this preparation. The elution is not symmetrical.

FIG. 1E is an elution curve from an ethyl alcohol fractionated IgG that has been degraded by plasmin activated during the fractionation procedure. While there is a reduced amount of aggregates, 27% of the total protein consists of IgG fragments with a molecular weight of around 52,000 Daltons. The ethyl alcohol precipitated plasmin degraded preparation shows both aggregates and fragments. This method of treating alcohol fractionated IgG with plasmin has been attempted and materials of this type have been tested clinically to determine their suitability for intravenous administration. It is difficult to control the amount of proteolysis. It is also clear from published studies that plasmin degraded material is cleared very rapidly from the circulation so that large doses of material must be administered to achieve therapeutic levels.

FIG. 1F represents Biogel elution curve of an EtOH precipitated IgG analyzed in two ways-first, total protein to determine the distribution of various molecules, and second, concentration of the various peaks in terms of IgG, A and M. The IgG, A and M content of each fraction was determined by diffusion in Mancini plates and a curve constructed from data derived from this information. As it can be seen, the high molecular weight aggregates as well as the tetramers, dimers, trimers, are all composed of IgG and not contaminating proteins.

This type of structural analysis demonstrates the extreme susceptibility of the human IgG molecule to alteration by a number of currently practiced isolation procedures. Precipitation of IgG with ethyl alcohol, chemical modification with $\beta$ propiolactone, and reduction and alkylation of the molecule all result in significant quantities of aggregates. (See Table I for comparison with native IgG.) In addition, there is evidence that these procedures result in marked shape changes as is reflected by the asymmetry of the elution curve, of the main 160,000 molecular weight components. Since both fragments and aggregates are eliminated from the circulation within minutes, there is also a drastic reduction in the quantity of 160,000 molecular weight molecules that would remain in the circulation and have some beneficial effect. The altered shape and the significant aggregation is strong supporting evidence that these fractionation procedures result in extensive denaturation of the IgG molecule.

THIN-LAYER POLYACRYLAMIDE GEL ISOELECTRIC FOCUSING OF IgG: COMPARISON OF NATIVE IgG WITH CHEMICALLY ALTERED, STRUCTURALLY MODIFIED, AND DENATURED IgG

Proteins in solution have an electric charge. When these solutions are placed between two electrodes connected to a source of direct current, the proteins will migrate to the electrode of opposite charge. Thus, positively charged ions migrate to the cathode and are therefore termed cations, and negatively charged ions migrate to the anode and are termed anions. Generally proteins migrate to the cathode in acid solutions and toward the anode in alkaline solutions. There exists a pH value at which a given protein would not move toward either electrode. This pH or pI is defined as the isoelectric point and is a constant which can aid in the characterization of the protein. Isoelectric focusing is a very high resolution technique for the separation of proteins according to their isoelectric properties. Because of their heterogeneity, immunoglobulins and IgG in particular have broad isoelectric pH ranges rather than a narrow point such as would be the case for a homogeneous protein like serum albumin. However, even with the broad ranges, this method can be used to characterize most particularly the IgG's that have been chemically modified in preparation. When these chemical modifications alter the number of charged groups on the protein molecule, this is reflected by a new isoelectric point range. The method also is very sensitive in detecting alterations that contribute to the heterogeneity of immunoglobulins. The heterogeneity of pooled native IgG when focused results in a broad isoelectric spectrum of what appears to be homogeneous protein (with broad rather than sharp narrow bands). When the IgG has been modified, either chemically or broken down structurally to fragments, this introduces an additional type of heterogeneity—a microheterogeneity generated by alteration of the native IgG and is reflected by the introduction of a number of sharply defined narrow bands of various isoelectric points.

Analytical isoelectric focusing has been performed in polyacrylamide gel. The gel matrix stabilizes the pH gradient against convection. Polyacrylamide gel has most of the properties needed as a support for electrofocusing. It is desirable that the gel have a sufficiently large pore size to permit free passage of the proteins during focusing. The polyacrylamide gel for the electrofocusing to be described was cast in a 2 mm layer on glass plates.

During isoelectric focusing, proteins migrate electrophoretically in a stationary pH gradient generated by a number of low molecular weight ampholytes of varying IEP's. A steady state is reached in which sample proteins are concentrated or focused as bands at their isoelectric point. The gel used in this experiment (LKB 1804-101) contains a polyacrylamide concentration of 5%, an ampholyte concentration of 2.4% (w/v), is 3% crosslinked and is $235 \times 90 \times 1$ mm in size. An LKB 2117 Multiphor unit is used in this experiment along with an LKB 2103 power supply. Filter paper tabs ($5 \times 10$ mm—Whatman, Paratex) containing 20 $\mu$l of sample (0.1 mg protein) are used for sample application. The $\beta$ propiolactone IgG was applied near the cathode while the remaining samples were applied near the anode. The samples were focused at 4° C. for 90 minutes at a constant 30 watts. The application tabs were removed after 45 minutes and the pH gradient of the gel at 4° C. determined at the end of the run. The pH is determined every 10 mm using a Beckman 3500 meter with a 5 mm combination electrode (Beckman 39505). The pH of the plate ranges from 4.9 to 8.9. The plate is refocused for 10 minutes and then the proteins are fixed by placing the gel in a solution containing 1% methanol (v/v) and 0.5% sulphosalicyclic acid (w/v) for 45 minutes. Prior to staining, the plate is soaked in destaining solution (25% ethanol [v/v] and 8% acidic acid [v/v]) for five minutes. This step allows the plate to equilibrate to staining conditions and allows for the complete removal of ampholytes from the gel. The plate is stained for 10 minutes at 60° C. in a filtered preparation containing 0.1% (w/v) Coomassie Blue R-250 dye in destaining solution. The plate is destained for at least 48 hours with several changes of destain.

The isoelectric range of various preparations of human IgG is presented in Table II. Note that the native IgG sample #5 has a pI range of pI 6.4-8.8. The $\beta$ propiolactone treated IgG sample #1 with pI range of 5.6-7.2 demonstrates that there has been significant chemical modification of surface charge markedly altering the pI range from the native state. The reason for this is that $\beta$ propiolactone reacts with carboxyl, amino, hydroxyl, sulphydryl, and phenolic groups of proteins. EtOH purification of IgG has a somewhat nearer range than the native material; however, the EtOH plasmin degraded sample #6 has the broadest range of 6.18-8.8.

The polyacrylamide focused gel from which these ranges were derived demonstrates another feature of this type of an analysis, namely the micro-heterogeneity of each preparation. There are two procedures which introduce significant micro-heterogeneity to the IgG-$\beta$ propiolactone treatment sample #1 and plasmin degradation sample #6. The sharp dense bands in the plasmin treated sample are derived from fragmentation of the aggregates and degradation of some of the 160,000 molecular weight molecules and contribute to the heterogeneity seen here. These fragments would of course be cleared very rapidly from the circulation and would not be there for therapeutic effect. The $\beta$ propiolactone treated IgG demonstrates the most marked alterations of the molecule both in IEP and in micro-heterogeneity. What effects these would have on introduction in the host is not clear. However, one would expect an impairment of some of the effector functions of the molecule and significantly reduced half-life in the circulation. In addition, alteration of surface charges by $\beta$ propiolactone indicate the native groups have been replaced by foreign chemical groupings, charges modified, and could post added hazards by introduction of foreign antigenic determinants that could well generate antibody which would react with the $\beta$ propiolactone treated molecule.

TABLE I

MOLECULAR SPECIES IN DIFFERENT HUMAN IgG PREPARATIONS: COMPARISON OF AGGREGATES, MONOMERS, AND FRAGMENTS WITH NATIVE IgG

| Preparation | Aggregates >300,00 MW % | Monomers 160,000 MW % | Fragments 50,000 MW % |
| --- | --- | --- | --- |
| Native human IgG IV | <1 | 99 | <1 |
| Reduced & Alkylated IgG IV | 20 | 80 | <1 |
| $\beta$ propiolactone IgG, IV | 14 | 83 | 2.5 |
| EtOH IgG, IM | 16 | 84 | <1 |
| EtOH plasmin IgG, IM | 7 | 63 | 27 |

2 ml sample applied to 2.6 × 94 cm Biogel A 1.5 column Protein concentration 45 mg/ml, Total Protein applied 90 mg

TABLE II

ISOELECTRIC RANGE OF VARIOUS PREPARATIONS OF HUMAN IgG

| Sample # | Preparation | pI Range |
| --- | --- | --- |
| 1 | $\beta$ propiolactone IgG, IV preparation | 5.6–7.2 |
| 2 | Reduced & Alkylated IgG, IV preparation | 6.5–9.0 |
| 3 | EtOH IgG, IM preparation$_1$ | 6.7–8.7 |
| 4 | EtOH IgG, IM preparation$_2$ | 7.0–8.8 |
| 5 | Native human IgG, IV preparation | 6.4–8.8 |
| 6 | EtOH plasmin IgG, IM preparation | 6.18–9.43 |

Sample protein concentration 5.0 mg/ml Total volume 20 μl, 0.1 mg total protein

IMMUNOELECTROPHORETIC ANALYSIS

Immunoelectrophoresis can demonstrate a number of factors, but for this study its purpose was to demonstrate two features—first, if there were any changes in the electrophoretic mobility of the gamma globulin suggesting chemical modification, and second, if there were any impurities present in the gamma globulin. Although this method is not the most sensitive for detecting impurities, it is possible to pick up contaminants that are present in microgram quantities.

In immunoelectrophoresis two methods are combined, gel electrophoresis followed by immunodiffusion. A buffered, agarose gel is used as the medium and the two steps of analysis are performed sequentially. Buffered agar is poured onto a horizontal glass plate to a uniform thickness. Following solidification and curing, a longitudinal center trough is cut out in the midline and a well punched out on either side of the trough for electrophoresis of the serum sample. After the serum is placed in the center well, it is separated under the influence of an electric field, and the charged protein particles migrate. Among the factors governing the migration may be the charge, size and shape of the particles, the concentration, ionic strength, pH of the solvents, the temperature and the viscosity of the medium, and the character and intensity of the electrical field. Following 80 minutes at 150 volts at which time it has been found that the proteins under analysis have all reached desirable separation, the slide is taken out of the electric field and an antisera specific to either human gamma globulin or whole human serum protein is added to the center trough and allowed to diffuse into the agar and react with each one of the separated plasma protein constituents. Following a 24 hour period for equilibrium and diffusion of the antisera into the gels, the gels are then washed with saline for a 48 hour period to remove any unreacted protein, then stained with an amido black dye, dried and photographed.

ELECTROPHORETIC MOBILITY

Electrophoretic mobility and impurities contaminating various IgG preparations can be visually compared with native IgG in the human plasma. Immunoelectrophoresis of the samples against an antisera was observed which reacts only with human IgG. The electrophoretic mobility of native IgG sample #4 and plasma IgG samples #6 and #7 were compared with the other IgG preparations. Samples were all at a protein concentration of 10 mg/ml. Sample #1 contained the $\beta$ propiolactone treated IgG and had clearly altered electrophoretic mobility whereas the reduced and alkylated sample #2, the ethyl alcohol samples #3 and #5 showed relatively similar electrophoretic mobility to the native IgG and the IgG in plasma. The alteration of the electrophoretic mobility of the $\beta$ propiolactone treated IgG would be expected from the demonstrated changes in IEP.

The precipitation bands from the immunodiffusion part of the immunoelectrophoresis performed with anti-human IgG showed only the presence of the IgG in each preparation including whole human plasma. To demonstrate the presence of other proteins or impurities in each sample the immunodiffusion part of the immunoelectrophoresis must be performed with anti-human whole serum. The anti-whole serum antibody is added to the trough because it contains antibodies to at least 30 different human plasma proteins and can therefore be used to determine impurities in each sample. The sample protein concentration in one experiment was 10 mg/ml in order to demonstrate the complexity of proteins in plasma while the sample protein concentration in a parallel companion experiment was 40 mg/ml to demonstrate the extent of impurities in each of the IgG preparations. It was shown that in addition to the introduction of additional negative charges, that the $\beta$ propiolactone treated IgG sample #1 contains a significant contamination with another anodally migrating protein. Sample #2, the reduced and alkylated IgG, shows splitting of the main IgG band indicating partial fragmentation.

Where the protein concentration of the sample had been increased to 40 mg/ml, we see better the extent of contaminating proteins in the various IgG preparations. The β propiolactone treated IgG sample #1 contains in addition to the two major components at least two other protein arcs adjacent to the well. Sample #2, the reduced and alkylated IgG, also is contaminated with these anodally migrating proteins including a band near the well. Sample #3, ethyl alcohol precipitated human IgG preparation, contains small quantities of the anodally migrating component plus some splitting of the main band and two additional minor bands near the well. The native IgG (sample #4) can be seen as homogeneous and consists of IgG. The fifth well contains another ethyl alcohol treated ethyl alcohol human IgG indicating less contamination than in the other preparations. It is to be noted that there is some variation from manufacturer to manufacturer in these proteins and that some practice a higher degree and more sophisticated art than others.

The immunoelectrophoretic analysis of the different IgG preparations confirms the fact that β propiolactone isoelectric point alterations are reflected in changes in electrophoretic mobility. In addition it demonstrates that the reduced and alkylated as well as some of the alcohol fractionated material contain a splitting of the IgG main band and more importantly that with the exception of the native IgG, these other preparations contain varying degrees of contaminants, from those present in milligram quantities to those detectable in microgram quantities. It is to be anticipated that because of the relative impurity that there are a number of other undetectable contaminants present in nanogram levels in these preparations.

QUALITATIVE ASSESSMENT OF THE EXTENT OF THE DENATURATION OF IgG: COMPARISON OF EtOH PREPARED IgG WITH NATIVE IgG-DETERMINATION OF DENATURATION BY SUSCEPTIBILITY TO LIMITED PROTEOLYSIS BY PLASMIN

Proteins, particularly those that exhibit characteristic biologic activity as enzymes, immunoglobulins, and IgG in particular, usually lose some if not all activity on denaturation. Denaturation may be caused in various ways. Among these are heating, treating with acid, alkali, or organic solvents such as ethyl alcohol, and finally concentrated solutions of salt or dilute concentrations of protein in solution. All these treatments will cause an alteration in the solubility properties of most proteins, but proteins show a wide difference in sensitivity to any one of these methods of denaturation. In practice if treatment is not unduly prolonged, the denaturation may be reversed by restoring the condition at which the protein is stable; therefore, we can distinguish between reversible and irreversible denaturation of proteins. In theory all denaturation is reversible.

The change in shape and the presence of aggregates on Biogel elution heretofore described for different IgG's, suggested that the IgG's were altered and denatured by methods of isolation and purification. A more precise and quantitative method of determining the extent of denaturation of IgG was therefore explored. Since the essential feature of the denaturation process of proteins is associated with an unfolding of tightly coiled peptide chains leading to the disorganization of the internal structure of the protein, we look for other means of determining denaturation other than decreased solubility, change of shape and greater asymmetry. It is well known that denatured proteins generally are more susceptible to the attack of proteolytic enzymes and native proteins. The unfolding of the native protein makes the peptide bond more accessible to enzymic action; therefore, one would expect denatured proteins to be more susceptible to the attack of proteolytic enzymes than the native proteins.

The method developed to quantitate the extent of denaturation of various IgG preparations for comparison with native IgG utilizes limited proteolysis with the enzyme plasmin. Plasmin is an endopeptidase and cleaves arginine-lysine or valine-isoleucine peptide bonds. The limited proteolysis test with plasmin was achieved by incubating at 37° C. a solution of each IgG preparation in a 0.05 M Tris HCl, 0.2 M NaCl, 0.02 M glycine buffer (pH 8.0) 0.5 ml with human plasmin enzyme solution 300 units containing 8.3 mg/ml of activated plasmin. The plasmin was activated by incubating with 2330 units of urokinase. The reaction of IgG and plasmin contained 105 mg IgG/2.5 mg plasmin, a ratio of 42. The reaction was stopped at 18 hours by freezing the samples at $-70°$ C. and then at a time when they could all be run together, they were eluted from a Biogel A 1.5 2.6×94 cm calibrated column. The effluent was collected in 7 mm aliquots and the optical density determined by adsorption at 280 millimicrons. The percent of protein in each of the peaks was calculated by determining the total area of the eluted peaks by planimetry and approximating areas of each peak's overlap.

Figure 2:
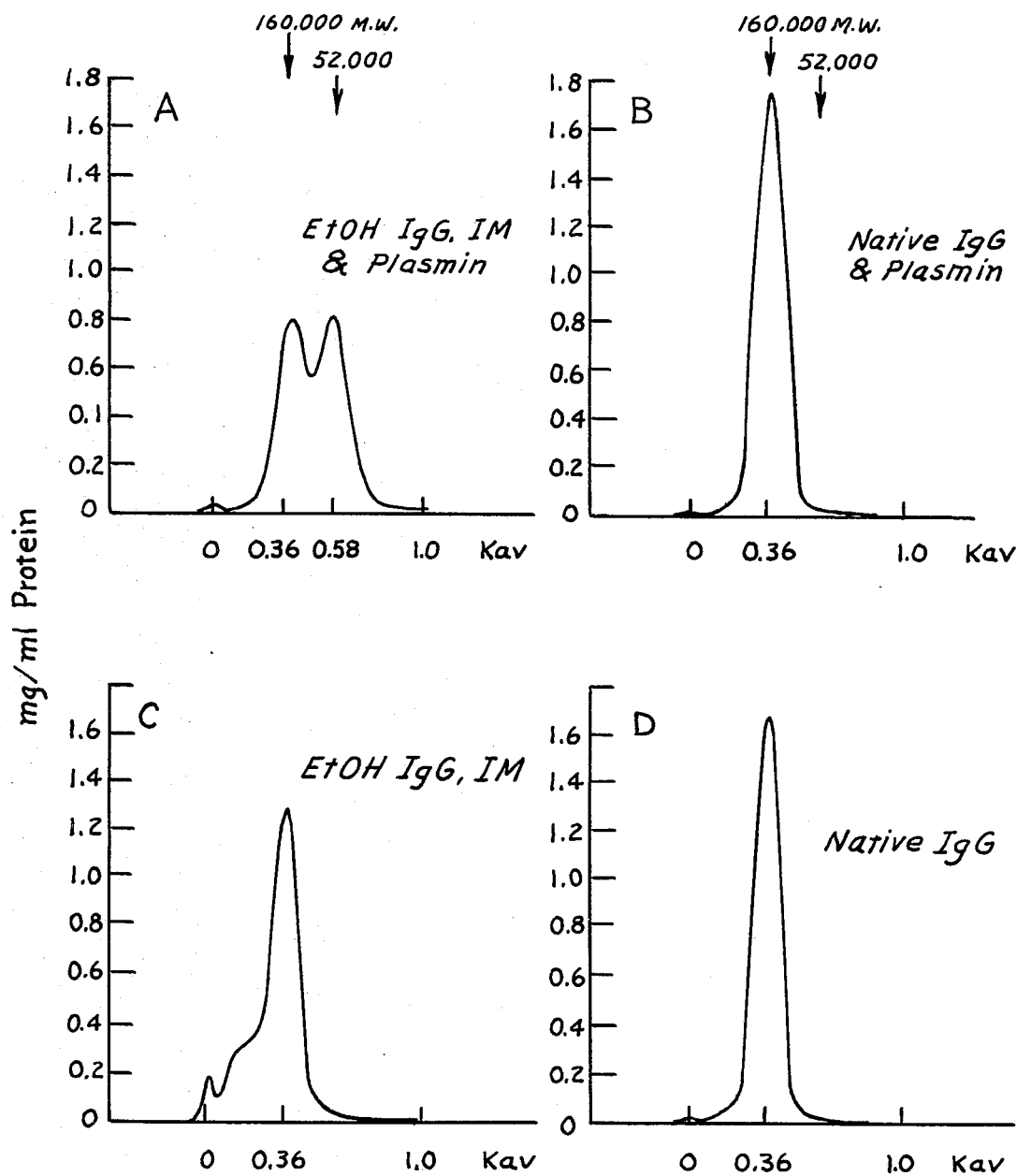
FIGS. 2A through 2D show the differential effect of plasmin on denatured IgG and native IgG.

The elution of protein from the Biogel A 1.5 column is illustrated in FIG. 2. Native IgG (FIG. 2D) incubated at 37° C. for 18 hours at a concentration of 45 mg/ml without plasmin elutes from the Biogel in a symmetrical, uniform peak of molecular weight of 160,000 Daltons, no aggregates nor fragments. Following limited proteolysis with plasmin (FIG. 2B), the native IgG appears unaltered, the peak is still symmetrical with little or no evidence of fragments or aggregates. This demonstrates that under conditions of this experiment the IgG preparation was not acted on by plasmin and therefore is a native IgG.

The elution of the EtOH IM IgG that was incubated for 18 hours at 37° C. with no enzyme is illustrated in FIG. 2C. There is extensive aggregation including dimers, trimers, and high molecular aggregates. The peak shows distinct asymmetry. Incubation of this IgG preparation with plasmin under the identical conditions as the native IgG is illustrated in FIG. 2A. Results of this study show the following: (1) disappearance of most of the aggregates, (2) the reduction in the main 160,000 molecular weight peak, and (3) formation of a second peak containing 52,000 molecular weight fragments of IgG. Quantitation of the differential effect of plasmin on EtOH IM IgG and native IgG is presented in Table III. Native IgG is resistant to limited proteolysis by plasmin whereas plasmin attacks and degrades the EtOH IM IgG. Aggregates which made up 13% of this preparation are attacked and end up as 52,000 molecular weight fragments. More significantly, the main 160,000 molecular weight peak is sensitive to plasmin proteolysis to the extent that 39% of this material is hydrolyzed and appears as the 52,000 molecular weight fragments. This is particularly informative since it confirms that the asymmetry of this peak that suggested denaturation clearly represents extensive unfolding of the polypeptide chains to the extent that plasmin now can attack and degrade this 160,000 molecular weight component since approximately 40% of the 160,000 molecules are now susceptible to proteolysis by plasmin. These are representative results of a number of experiments confirming that other methods of preparing IgG β propiolactone, reduction and alkylation, salting out, ethylene glycol precipitation denature the protein and render them susceptible to the attack by the proteolytic enzyme plasmin while the native IgG is unaffected.

TABLE III
DIFFERENTIAL EFFECT OF PLASMIN ON EtOH IM IgG AND NATIVE IgG

| Sample | Aggregates | 160,000 Peak | 52,000 Peak |
|---|---|---|---|
| EtOH IgG IM | 13% | 87% | less 1% |
| EtOH IgG IM + Plasmin | 1% | 48% | 51% |
| Percent 160,000 peak attached by plasmin | | 39% | |
| Native IgG | less 1% | 99% | 0% |
| Native IgG + Plasmin | 0% | 98% | 1% |
| Percent 160,000 Peak attached by plasmin | | 1% | |

IN VITRO ASSESSMENT OF ALTERED BIOLOGIC EFFECTOR FUNCTIONS OF VARIOUS IgG PREPARATIONS COMPARED WITH NATIVE IgG: ANTI-COMPLEMENTARY ACTIVITY AS AN INDICATION OF DENATURATION

In its normal state in blood, IgG does not interact appreciably with components of the complement system. The biologically active sites within the FC region ($C_{\gamma 2}$ domain) of IgG that interact with complement are expressed or exposed as a result of conformational or structural changes that normally result following specific antigen/antibody combination with surface antigens on bacteria, viruses, altered cells. Results of this combination normally mediate many aspects of inflammation and facilitate ingestion of pathogens by phagocytes. Once the site in the FC region ($C_{\gamma 2}$ domain) is exposed, the first component of complement Cl attaches through a non-covalent linkage or ionic bond and results in enzymatic activation of the complement cascade. Structural alterations of the IgG resulting from denaturation by solvent precipitation such as aggregate formation also expose these biologically active complement fixing sites. Therefore the extent of complement fixation or anti-complementary activity of IgG can be used as a measurement of denaturation and alterations from the native state.

It was observed in 1944 that fractionated IgG was anticomplementary. Subsequently in 1945, it was demonstrated that aggregates in the fractionated IgG were responsible for this effect. Later in 1959 it was shown that heat denatured (aggregated) IgG fixed complement in a manner indistinguishable from that of antigen/antibody complexes.

The methods used in these studies to compare the anticomplementary activity of various IgG preparations with native IgG involved the determination of the quantity in micrograms of IgG protein required to fix 50% of a standard preparation of Cl complement. Comparisons were made of anti-complementary activity of human IgG preparations with native IgG by determining the micrograms of IgG protein required to fix 50% of Cl. Table IV shows results of these determinations. With the exception of the EtOH plasmin IgG IM preparation, there is a direct relationship between the aggregate concentration and the anti-complementary activity. This is particularly noteworthy since plasmin degradation removes aggregates and reduces anti-complementary activity. This method has been used in the preparation of intravenous IgG. However, there have been many problems associated with this because the extent of degradation of the main 160,000 molecular weight IgG cannot be adequately controlled. This results from the fact that the main peak is also extensively denatured as heretofore shown. The EtOH Red Cross IgG containing 30% aggregates was the most active in fixation of Cl complement since only 0.15 microgram fixed 50% of the complement. Also of interest is the fact that while there is a direct general relationship between the extent of aggregation and the anti-complementary activity, the quantity of the EtOH reduced and alkylated IgG IV for fixation of complement required twenty times the quantity of protein for 50% complement consumption. The purpose of reduction and alkylation of this IgG was to reduce its anti-complementary activity and this is demonstrated and supported by these studies. However, the native IgG has significantly less anti-complementary activity (400-fold less) than any of the other preparations. These analyses add further support to the fact that a great number of fractionation procedures produce denaturation in the IgG molecule, particularly when compared to a native IgG. These observations are consistent with the view that there have been extensive alterations in the structure of these molecules, particularly in the FC region that result in exposing the biologically active complement fixing sites and provide information explaining why on intravenous administration these preparations of altered, denatured IgG produce significant systemic reactions, one of which involves the activation of the complement cascade. It should be noted that plasmin degradation, reduction and alkylation, and β propiolactone treatment of IgG reduce its anti-complementary while there are still appreciable quantities of aggregated IgG. Complement fixation therefore has some limitations in assessing denatured IgG.

TABLE IV
COMPARISON OF ANTI-COMPLEMENTARY ACTIVITY ($C^1$ BINDING) OF HUMAN IgG PREPARATIONS WITH NATIVE IgG

| Preparations | Molecular Size | Percent Aggregation | Anti-Complimentary Activity* |
|---|---|---|---|
| EtOH IgG Red Cross | 160,000 (69%) | 30% | 0.15 |
| EtOH IgG IM | 160,000 (84%) | 16% | 0.44 |
| EtOH-Reduced & Alkylated IgG IV | 160,000 (80%) | 20% | 8.00 |
| EtOH-plasmin IgG IM | 160,000 (63%) 52,000 (27%) | 7% | 22.00 |
| Native IgG IV | 160,000 (99%) | less 1% | 500.00 |

*µg Protein required to fix 50% $C_1^1 q$.

PHARMACOLOGICALLY ACTIVE IMPURITIES IN HUMAN IgG PREPARATIONS: COMPARISON OF NATIVE IgG WITH HUMAN IgG PREPARED BY CONVENTIONAL METHODS

Components of the fibrinolytic, coagulation and kininogen systems of plasma are activated during fractionation by ethyl alcohol precipitation, ethylene glycol precipitation, salt precipitation, and by DEAE chromatography. Because these activated components are not removed during fractionation, they appear in nanogram quantities in the final IgG product. However, due to their potent activity, they nonetheless have been implicated in the production of flushing, erythema, and hypotension leading to circulatory collapse when the IgG is injected intravenously. The native IgG product prepared by the method described in my aforesaid application Serial No. 829,565 does not produce any of these above reactions on intravenous administration and therefore is presumed to be free of these contaminants. There are two demonstrable reasons why this is the case: (1) the precursors of the fibrinolytic, coagulation and kininogen systems are removed by the silica dioxide ($SiO_2$) treatment of plasma before fractionation on QAE, and (2) the elution pH of the QAE ion exchange procedure retains proteins and peptides and the IEP range of these activated fragments (pI of 4.2–4.6). Table V shows results of treating plasma with 40 grams/liter of silica dioxide. The pretreated plasma contains normal levels of the various precursors including the following: fibrinogen, plasminogen, factor XII (Hagamen factor), prekallikrein system, and the complement components. The post-silica dioxide treatment plasma is without detectable levels of these factors.

It has been proposed that the flushing, erythema, and hypotension result from the presence of Hagamen factor fragments (prekallikrein activator PKA) which by acting enzymatically on prekallikrein, continue to generate bradykinin in the patient in excess of that being inactivated. The following scheme illustrates part of the proposed mechanism:

MECHANISM FOR INDUCTION OF HYPOTENSION BY PKA ACTIVATOR IN IgG PREPARATIONS

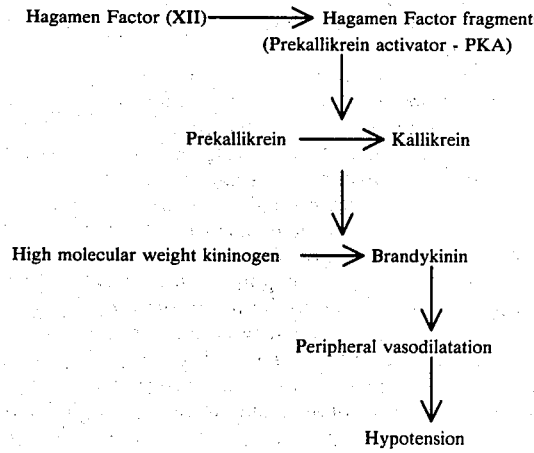

TABLE V

REMOVAL OF THE COMPLEMENT, COAGULATION AND KININOGEN COMPONENTS OF PLASMA WITH $SiO_2$

|  | Plasma | Post $SiO_2$ treated plasma |
|---|---|---|
| Total protein | 64 mg/ml | 70 mg/ml |
| Fibrinogen | 300 mg % | 0 |
| Plasminogen | 12 mg % | 0 |
| β-lipoprotiens | 420 mg % | 0 |
| HDL associated HLA antigens | Present | Not detected |
| Cholesterol | 160 mg % | 0 |
| Triglycerides | 100 mg % | 50 mg % |
| Clotting Factors | Percent Normal Activity | |
| II | 100% | 100% |
| V | 100% | 0% |
| VII | 100% | 0% |
| VIII | 100% | 0% |
| XI | 100% | 0% |
| XII (Hageman Factor) | 100% | 0% |
| Hemolytic C (screen) | Normal | No lysis |
| Hemolytic C (quant.) | 24 units/ml | Not detected |
| $C_4$ | 480 μg/ml | <10 |
| $C_3$ | 1200 μg/ml | <30 |
| C1q | 194 μg/ml | Not detected |
| $C_5$ | 112 μg/ml | " |
| Properdin | 13.6 μg/ml | " |
| $C_3PA$ | 187 μg/ml | " |
| Prekalikrein | 84* μmole/hr/ml | 0* |

*Kaolin activated

Table VI shows results of analysis for prekallikrein activity of native IgG and other IgG preparations. The native IgG was prepared by the method of my earlier application. It can be seen that the ethyl alcohol IgG preparation and the reduced and alkylated intravenous IgG both contain significant quantities of prekallikrein activator activity, while the native IgG and the β propiolactone preparations are essentially free of this activity.

INTRAVENOUS INJECTIONS OF NATIVE IgG AND OTHER ALTERED IgG PREPARATIONS: INCIDENCE OF SEVERE REACTIONS AND CIRCULATORY HALF-LIFE

Intravenous injection of fresh human plasma is safe and not associated with adverse reactions. The IgG present in fresh plasma has a circulatory half-life following intravenous injection of 24–32 days. Therefore, a native IgG preparation should be expected to possess similar characteristics upon intravenous administration. All priorities have been concentrated first on IgG preparations safe for intravenous administration with secondary emphasis on circulatory half-life. However, a native IgG preparation which combines safety and half-life comparable to IgG in fresh plasma would provide maximal benefits to the patients, namely safety and maximal therapeutic efficacy. The preceding sections have been devoted to studies determined to elucidate the many effects of various fractionation procedure in introducing structural alterations in the IgG isolated. Whether these documented, irreversible alterations from the native state result in decreased circulatory half-life and the production of severe adverse reactions will be addressed in this final section. Table VII compares the circulatory half-lifes following intravenous administration of various IgG preparations. IgG contained in fresh normal plasma has a half-life of 24–32 days, while the half-life of native IgG is from 24–27 days. All other preparations have significantly reduced half-lifes. Plasmin degraded IgG fragments' half-lifes range from 5 hours for the FAB fragments, 8-10 days for the FC fragment, and 18-20 days for the intact 160,000 molecular weight component. Alterations of surface groups, surface charge, isoelectric point, electrophoretic mobility, micro-heterogeneity, and aggregation by β propiolactone treatment of IgG result in circulatory half-life of 14 days. These reductions in circulatory half-life significantly reduce therapeutic activity of IgG. For example, the reduction from 28 days to 14 days in half-life would reduce the therapeutic index by a factor somewhat greater than 2. This would require twice the dose of IgG to achieve comparable therapeutic effects of a native IgG preparation.

TABLE VI
PREKALLIKREIN (PKA) ACTIVITY OF NATIVE IgG AND OTHER IgG PREPARATIONS

| Preparation | PKA activity (% of reference) |
|---|---|
| Native IgG | <1 |
| EtOH IgG IM | 62 |
| Reduced & Alkylated IgG IV | 90 |
| β propiolactone IgG IV | <1 |
| Reference | 100 |

TABLE VII
CIRCULATORY HALF-LIFE OF VARIOUS HUMAN IgG PREPARATIONS FOLLOWING INTRAVENOUS ADMINISTRATION

| Preparation | Half-life (T1/2) |
|---|---|
| Fresh plasma (IgG) | 24-32 days |
| EtOH plasmin IgG | |
| Intact IgG | 8-20 days |
| FC fragment | 8-10 days |
| FAB fragment | 5 hours |
| β propiolactone IgG | 4-12 days |
| Native IgG | 23-27 days |

INCIDENCE OF ADVERSE REACTIONS

The high incidence of severe adverse reactions on intravenous administration of the licensed ethyl alcohol IgG has prevented administration by this route. The incidence of these reactions is presented in Table VIII. Depending on the patient population, reactions can vary from 92% in immune deficiency syndrome patients to 13% in normal healthy individuals, whereas normal plasma is not productive of reactions in either group. β propiolactone treatment of IgG reduces significantly the incidence of severe reactions in immune deficiency patients (from 92% to 15%). Intravenous administration of native IgG however approaches fresh plasma in almost complete absence of reactions. We conclude that the added efforts required to prepare an undenatured, monomeric, native IgG results in definite benefits to the patient. These include safety, significantly greater therapeutic index by virtue of the near normal circulating half-lifes.

TABLE VIII
INCIDENCE OF SEVERE REACTIONS ON INTRAVENOUS ADMINISTRATION OF VARIOUS IgG PREPARATIONS

| Preparations | # Patients | % Reactions |
|---|---|---|
| Normal Fresh Plasma Immune deficiency syndrome patient | 26 | none |
| Native IgG Patients with life threatening infection | 107 | <1% |
| β propiolactone IgG Immune deficiency syndrome patient | 12 | 15% |
| EtOH IgG Normal, healthy patient | 55 | 13% |
| Immune deficiency syndrome patient | 15 | 92% |

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. An isolated natural, unaltered, unfragmented, undenatured monomeric immune gamma globulin for intravenous administration characterized by 99% purity and containing less than 1% aggregates and less than 1% dissociated materials.

2. Purified gamma globulin according to claim 1 further characterized by molecular weight of 160,000 Daltons with no high molecular weight aggregated IgG and no low molecular weight IgG fragments.

3. Purified gamma globulin according to claim 1 further characterized by native electrophoretic ranges.

4. Purified gamma globulin according to claim 1 further characterized by native isoelectric point ranges between about 6.4 and 8.8.

5. Purified gamma globulin according to claim 1 further characterized by resistance to proteolysis with plasmin.

6. Purified gamma globulin according to claim 1 further characterized by low anti-complementary activity.

7. Purified gamma globulin according to claim 1 further characterized by normal circulatory half-life of at least about three weeks following intravenous administration.

8. Purified gamma globulin according to claim 1 further characterized by freedom from properties activating the complement pathway, blood coagulation and kininogen system.

9. An isolated natural, unaltered, unfragmented, undenatured monomeric immune gamma globulin for intravenous administration characterized by 99% purity and containing less than 1% aggregates and less than 1% dissociated materials, having molecular weight of 160,000 Daltons with no high molecular weight aggregated IgG and no low molecular weight IgG fragments, and further characterized by native electrophoretic ranges, native isoelectric point ranges between about 6.4 and 8.8, resistance to limited proteolysis with plasmin, low anti-complementary activity, normal circulatory half-life of at least about three weeks following intravenous administration, and freedom from properties activating the complement pathway, blood coagulation and kininogen system.

* * * * *

UNITED STATES PATENT AND TRADEMARK OFFICE
CERTIFICATE OF CORRECTION

PATENT NO. : 4,296,027
DATED : October 20, 1981
INVENTOR(S) : RICHARD M. CONDIE It is certified that error appears in the above-identified patent and that said Letters Patent is hereby corrected as shown below:

Col. 1, line 9,

--- The present invention was made with the support of Grant No. AM13083 and AI06589 from the National Institutes of Health. The Government has certain rights in the invention. ---

Signed and Sealed this

Fourteenth Day of January, 1997

Attest:

BRUCE LEHMAN

Attesting Officer

Commissioner of Patents and Trademarks